United States Patent
Murugesan

(10) Patent No.: US 10,772,627 B2
(45) Date of Patent: Sep. 15, 2020

(54) STAPLER WITH AUTO-MATIC LOCKOUT MECHANISM

(71) Applicant: Covidien LP, Mansfield, MA (US)

(72) Inventor: Ganesan Murugesan, Minhang District (CN)

(73) Assignee: Covidien LP, Mansfield, MA (US)

(*) Notice: Subject to any disclaimer, the term of this patent is extended or adjusted under 35 U.S.C. 154(b) by 456 days.

(21) Appl. No.: 15/535,072

(22) PCT Filed: Dec. 11, 2014

(86) PCT No.: PCT/CN2014/093575
§ 371 (c)(1),
(2) Date: Jun. 12, 2017

(87) PCT Pub. No.: WO2016/090600
PCT Pub. Date: Jun. 16, 2016

(65) Prior Publication Data
US 2017/0348002 A1 Dec. 7, 2017

(51) Int. Cl.
*A61B 17/00* (2006.01)
*A61B 17/072* (2006.01)
(Continued)

(52) U.S. Cl.
CPC .... *A61B 17/07207* (2013.01); *A61B 17/1155* (2013.01); *A61B 2017/00367* (2013.01);
(Continued)

(58) Field of Classification Search
CPC .......... A61B 2017/00367; A61B 17/08; A61B 17/282; A61B 2090/0807; A61B 17/072;
(Continued)

(56) References Cited

U.S. PATENT DOCUMENTS 3,193,165 A 7/1965 Akhalaya et al.
3,388,847 A 6/1968 Kasulin et al.
(Continued)

FOREIGN PATENT DOCUMENTS

CA 908529 A 8/1972
CA 2805365 A1 8/2013
(Continued)

OTHER PUBLICATIONS

Japanese Office Action dated Sep. 27, 2018 issued in JP Application No. 2017530594.
(Continued)

*Primary Examiner* — Thanh K Truong
*Assistant Examiner* — Patrick B Fry
(74) *Attorney, Agent, or Firm* — Carter, DeLuca & Farrell LLP

(57) ABSTRACT

A surgical stapling device (10) is provided that includes a handle assembly (12), a movable trigger (26) and an elongated body portion (14). A staple containing shell assembly (22) is mounted on a distal end of the elongated body portion (14) and an anvil assembly (20) is movably mounted relative to the staple containing shell assembly (22). An auto-lock safety mechanism (40) is provided to prevent secondary actuation of the surgical stapling device after initial actuation. The auto-lock safety mechanism (40) includes a primary lock or slider assembly (42) for blocking movement of the trigger (26) and a secondary lock or stopper (44) for blocking movement of the slider assembly (42) prior to approximation of the anvil assembly (20) relative to the staple containing shell assembly (22). A slider (70) is urged to a locked or blocking position by a biasing member (72).

6 Claims, 8 Drawing Sheets

(51) Int. Cl.
*A61B 17/115* (2006.01)
*A61B 90/00* (2016.01)

(52) U.S. Cl.
CPC .............. *A61B 2017/07257* (2013.01); *A61B 2017/07278* (2013.01); *A61B 2090/0814* (2016.02)

(58) Field of Classification Search
CPC .... A61B 2017/2912; A61B 2017/2917; A61B 2017/2919
USPC ........................................................ 606/143
See application file for complete search history.

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,378 A * | 5/1987 | Sturm .................. A44C 5/2047 24/116 A |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,513 A * | 9/1995 | Davison ............. A61B 17/1285 227/901 |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |

(56) References Cited

U.S. PATENT DOCUMENTS

| | | |
|---|---|---|
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,261,302 B1 * | 7/2001 | Voegele ............. A61B 90/39 606/142 |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,791,827 B2 * | 9/2004 | Kuo ............. G06F 1/1616 343/702 |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 * | 9/2005 | Gresham ............. A61B 17/115 227/175.1 |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,490,978 B2 * | 2/2009 | Crisci ............. G04B 19/283 368/294 |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |

(56) References Cited

U.S. PATENT DOCUMENTS

| | | | |
|---|---|---|---|
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,819,298 B2 * | 10/2010 | Hall ............... A61B 17/07207 227/176.1 |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 * | 2/2013 | Milliman ............... A61B 17/068 227/179.1 |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,364,235 B2 * | 6/2016 | Ranucci ............... A61B 17/10 |
| 9,364,958 B2 * | 6/2016 | Scimone ............... B26B 5/003 |
| 10,194,976 B2 * | 2/2019 | Boudreaux ........ A61B 18/1445 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0179063 A1 | 7/2009 | Milliman et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |

(56) References Cited

U.S. PATENT DOCUMENTS

| | | |
|---|---|---|
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0080332 A1 | 4/2012 | Shelton, IV et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0276963 A1* | 9/2014 | Ranucci ............. A61B 17/10 606/139 |
| 2015/0080916 A1* | 3/2015 | Aranyi ............. A61B 17/12 606/143 |
| 2016/0051317 A1* | 2/2016 | Boudreaux ........ A61B 18/1445 606/52 |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |

FOREIGN PATENT DOCUMENTS

| | | |
|---|---|---|
| CN | 103720500 A | 4/2014 |
| CN | 103800043 A | 5/2014 |
| CN | 103987331 A | 8/2014 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2002085415 A | 3/2002 |
| JP | 2004147969 A | 5/2004 |
| JP | 2007516730 A | 6/2007 |
| JP | 2013-138860 A | 7/2013 |
| JP | 2013542000 A | 11/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 2001/054594 A1 | 8/2001 |
| WO | 2008/107918 A1 | 9/2008 |

OTHER PUBLICATIONS

European Search Report dated Jun. 14, 2018 in EP Appln. No. 14907944.

International Search Report for PCT/CN2014/093575 date of completion is Feb. 6, 2015 (2 pages).

Chinese Office Action dated Jul. 29, 2019, issued in Chinese Appln. No. 201480083948.

* cited by examiner

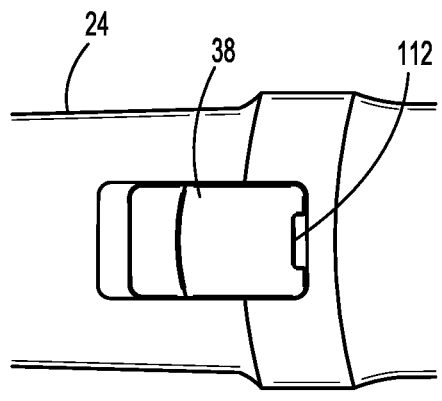 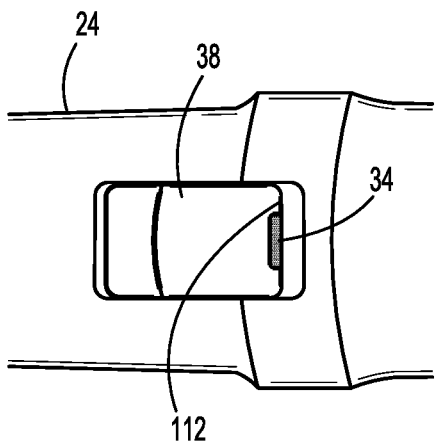
FIG. 9  FIG. 10
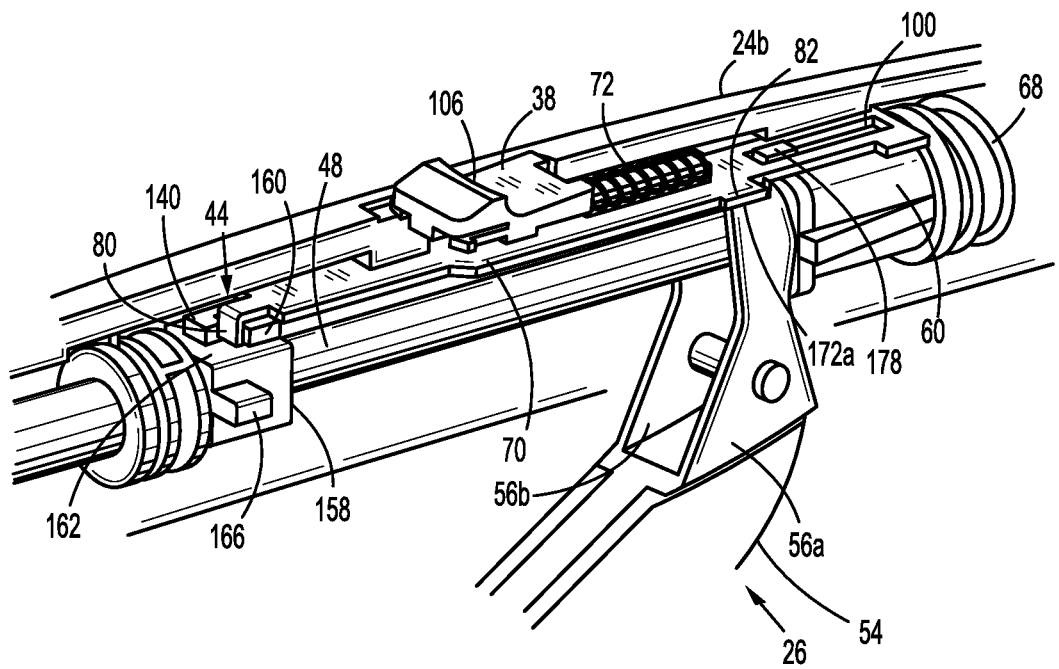
FIG. 11

STAPLER WITH AUTO-MATIC LOCKOUT MECHANISM

CROSS-REFERENCE TO RELATED APPLICATIONS

This application is a National Stage Application of PCT/CN2014/093575 under 35USC § 371 (a), the disclosure of the above-identified application is hereby incorporated by reference in its entirety.

BACKGROUND

1. Technical Field

The present disclosure relates to a surgical stapling device. More particularly, the present disclosure relates to a surgical stapling device having an automatic internal lock out mechanism to prevent re-firing of the surgical stapling device.

2. Background of Related Art

Surgical stapling devices and, in particular, circular surgical stapling devices, are often used to treat and remove hemorrhoids from within the rectum of a patient. Typically, an anvil assembly of the surgical stapling device is positioned in the rectum beyond the hemorrhoid and is connected to a staple containing shell of the surgical stapling device which is located forwardly of the hemorrhoid. Next, the hemorrhoidal and/or mucosal tissue is tied off to a center rod of the anvil assembly using purse string sutures and the anvil assembly is approximated to a position adjacent the staple containing shell to clamp the hemorrhoidal or mucosal tissue. Thereafter, the surgical stapling device is actuated by depressing a firing trigger of the surgical stapling device to eject staples from the staple containing shell and create a circular line of staples through tissue adjacent the hemorrhoid. Simultaneously, a circular knife excises the hemorrhoidal and/or mucosal tissue positioned within the staple containing shell inwardly of the staple line. The surgical stapling device containing the excised portion of the hemorrhoidal and/or mucosal tissue captured between the anvil assembly and the staple containing shell is then removed from the patient.

Various external lock out devices have been provided on surgical stapling devices to prevent inadvertent actuation of a firing trigger of a stapling device prior to use. These lockout devices include movable latches positioned between the firing trigger and a handle housing of the surgical stapling device which engage the firing trigger and prevent actuation of the firing trigger until the latch is manually moved to an unlocked position. While useful, these latches not only require manual manipulation to unlock the firing trigger but, more importantly, require manual operation to relock the firing trigger after the surgical stapling device has been fired.

In use, an operator may inadvertently reactuate the surgical stapling device prior to or during removal of the surgical stapling device from the patient or prior to resetting the manual external latch. Such an action could cause tissue damage and jeopardize the success of the surgical procedure.

Thus, there is a need for a surgical stapling device for use in the treatment of hemorrhoids as well as a variety of other procedures which includes lockout device to prevent premature actuation of the surgical stapling device. There is also a need for a surgical stapling device containing an internal automatic lock out mechanism which automatically prevents a second actuation of the surgical stapling device after initial firing.

SUMMARY

In one aspect of the present disclosure, a surgical stapling device is provided that includes a handle assembly having a stationary handle housing and a movable trigger mounted to the handle housing. An elongated body portion extends from the handle housing. A staple containing shell assembly is mounted on a distal end of the elongated body portion and an anvil assembly is movably mounted relative to the staple containing shell assembly. An approximation mechanism includes a rotatable approximation knob mounted on the stationary handle housing and a screw shaft assembly extending from the approximation knob to the anvil assembly. The approximation mechanism is configured such that rotation of the approximation knob effects translation of the screw shaft assembly within the handle assembly to move the anvil assembly from a first position spaced from the staple containing shell assembly to a second approximated position adjacent the staple containing shell assembly. A pusher extends through the elongated body portion from the handle housing to the staple containing shell assembly. The movable trigger is movable into engagement with the pusher such that movement of the movable trigger toward the stationary handle housing drives the pusher distally to drive staples out of the staple containing shell assembly and into the anvil assembly. A slider assembly is positioned within the handle housing and includes a slider and a biasing member. The slider is movable between a first position blocking the movable trigger from movement and a second position spaced from the movable trigger. The biasing member is positioned to urge the slider towards the first position.

In embodiments, the slider is longitudinally movable within the handle housing and includes at least one trigger block positioned to engage the movable trigger.

In certain embodiments, the biasing member includes a coil spring.

In some embodiments, the slider assembly includes a switch that is fixedly attached to the slider and extends through a window formed through the handle housing.

In embodiments, the slider includes a mount having an upright bar and a proximally extending arm and the switch is fixedly attached to a proximal end of the proximally extending arm. The coil spring is mounted around the proximally extending arm and engages the upright bar at a first end of the coil spring and the handle housing at a second end of the coil spring.

In certain embodiments, the switch includes at least one flexible latch that is configured to be received within a notch formed in an edge of the window in the handle housing when the slider assembly is in the second position to retain the slider assembly in the second position.

In embodiments, the slider includes a longitudinal slot and the pusher includes a protrusion movable within the longitudinal slot such that distal movement of the protrusion into engagement with one end of the longitudinal slot disengages the at least one flexible latch of the switch from the notch in the handle housing.

In some embodiments, the switch defines a notch. The switch covers an indicator of the handle housing when the slider is in the first position and reveals the indicator of the handle housing when the switch is moved towards the second position.

In another aspect of the disclosure, a surgical stapling device includes a handle assembly having a stationary handle housing and a movable trigger mounted to the handle housing. An elongated body portion extends from the handle housing. A staple containing shell assembly is mounted on a distal end of the elongated body portion and an anvil assembly is movably mounted relative to the staple containing shell assembly. A rotatable approximation knob is mounted on the stationary handle housing and a screw shaft assembly extends from the approximation knob to the anvil assembly such that rotation of the approximation knob moves screw shaft assembly from an advanced position to a retracted position to move the anvil assembly from a first position spaced from the staple containing shell assembly to a second approximated position adjacent the staple containing shell assembly. A pusher extends through the elongated body portion from the handle housing to the staple containing shell assembly and is engagable with the movable trigger such that movement of the movable trigger toward the stationary handle housing drives the pusher distally to drive staples out of the staple containing shell assembly and into the anvil assembly. A slider assembly includes a slider having a tab at a proximal end of the slider. The slider is positioned within the handle housing and is movable between a first position blocking the movable trigger from movement and a second position spaced from the movable trigger. A flexible stopper is positioned within the handle housing and is releasably engagable with the tab of the slider. A block is affixed to the screw shaft assembly and is movable longitudinally within the handle housing in response to rotation of the approximation knob. The block is engagable with the flexible stopper as the screw shaft assembly moves from the advanced position towards the retracted position to move the flexible stopper out of engagement with the tab of the slider to facilitate movement of the slider from the first position to the second position.

In embodiments, the stopper includes a first longitudinal bar mounted to the handle housing, a cross bar connected to the first longitudinal bar and a second longitudinal bar having a distal end connected to the cross bar. The second longitudinal bar includes a catch configured to releasably engage the tab of the slider.

In some embodiments, the block includes a projection having a cam edge that is engagable with the catch to move the catch out of engagement with the tab of the slider.

In certain embodiments, the catch includes an inwardly directed portion formed on the proximal end of the second longitudinal bar and a cam on the second longitudinal bar located distally of the inwardly directed portion. The cam and the inwardly directed portion define a gap configured to receive the tab of the slider.

In some embodiments, the cam includes an angled cam face which is positioned to engage the cam edge of the projection on the block.

In embodiments, the projection on the block is positioned to engage the tab on the slider such that proximal movement of the block moves the slider proximally. The slider assembly includes a switch which is positioned within a window of the handle housing over an indicator, wherein proximal movement of the slider effects movement of the switch to reveal the indicator through the window in the handle housing.

DESCRIPTION OF THE DRAWINGS

An embodiment of the presently disclosed surgical stapling device is disclosed herein with reference to the drawings, wherein:

FIG. 9 is a top plan view of a portion of the handle housing showing a safety button;

FIG. 10 is a top plan view, similar to FIG. 9, showing the safety button moved relative to the housing to reveal an indicator portion of the safety button;

FIG. 11 is a perspective view of the body portion of the surgical stapling device with half the handle housing removed and a trigger of the body portion blocked by the slider of the lockout assembly;

DETAILED DESCRIPTION OF EMBODIMENTS

An embodiment of the presently disclosed surgical stapling device will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Figure 1:
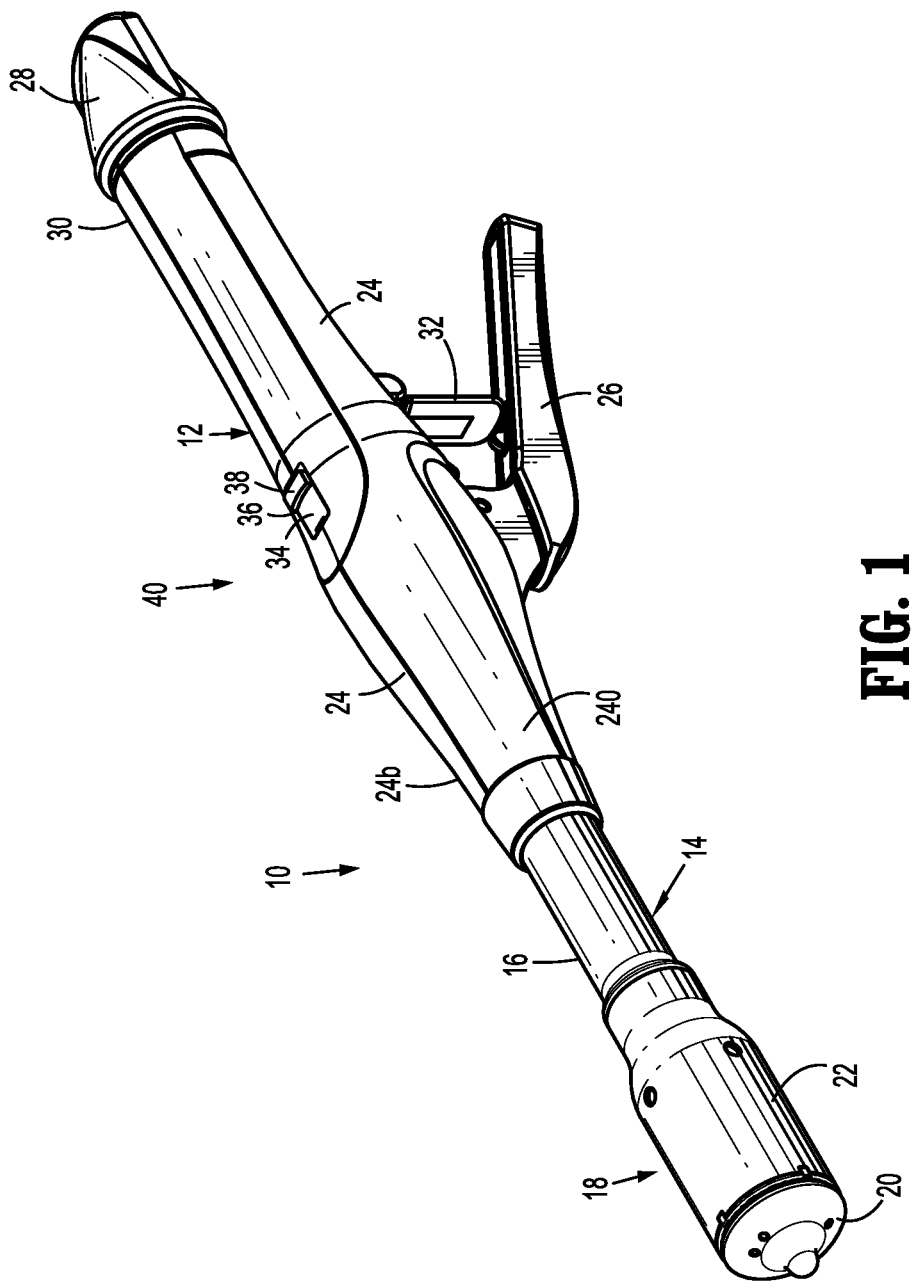
FIG. 1 is a perspective view of a surgical stapling device for use in hemorrhoidal surgery.

Referring initially to FIG. 1, there is disclosed a surgical stapling device 10 for use in hemorrhoidal surgery. Surgical stapling device 10 generally includes a handle assembly 12 and an elongated body portion 14 having an elongated outer tube 16 and a distal head portion 18.

Distal head portion 18 includes an anvil assembly 20 and a shell assembly 22 which are provided to approximate and staple tissues captured therebetween. While not specifically shown, anvil assembly 20 includes an anvil head containing staple clinching pockets and an anvil shaft for removable connection to elongated body portion 14. Likewise, while not specifically shown, shell assembly 22 includes a plurality of staples and pushers designed to drive the staples out of shell assembly 22, through tissue and into the staple clinching pockets of anvil assembly 20 in a manner commonly known in the art.

Handle assembly 12 generally includes a stationary handle housing 24 extending proximally from elongated body portion 14, a movable or firing trigger 26 pivotally mounted to handle housing 24 and a rotatable approximation knob 28 positioned on a proximal end 30 of handle housing 24. Actuation of rotatable approximation knob 28 functions to move anvil assembly 20 relative to shell assembly 22 to capture tissue therebetween as is known in the art. See, e.g., U.S. Pat. No. 7,303,106 to Milliman et al. ("the '106 patent") which is incorporated herein by reference in its entirety. In embodiments, an external, manually actuated trigger latch 32 is pivotally mounted on handle housing 24 and engagable with firing trigger 26 to block movement of firing trigger 26. Handle housing 24 is formed as two joined handle housing halves 24a and 24b. In the presently disclosed stapling device 10, the trigger latch 32 is optional and can be discarded.

Surgical stapling device 10 additionally includes an indicator 34 that is, visible through a window 36 formed in handle housing 24, and provides a visual indication of the degree of approximation of the anvil assembly 20 relative to shell assembly 22. A safety button or switch 38 is movable within window 36 and is associated with an auto-lock safety mechanism 40 described in more detail hereinbelow.

Figures 2, 3, 3A:
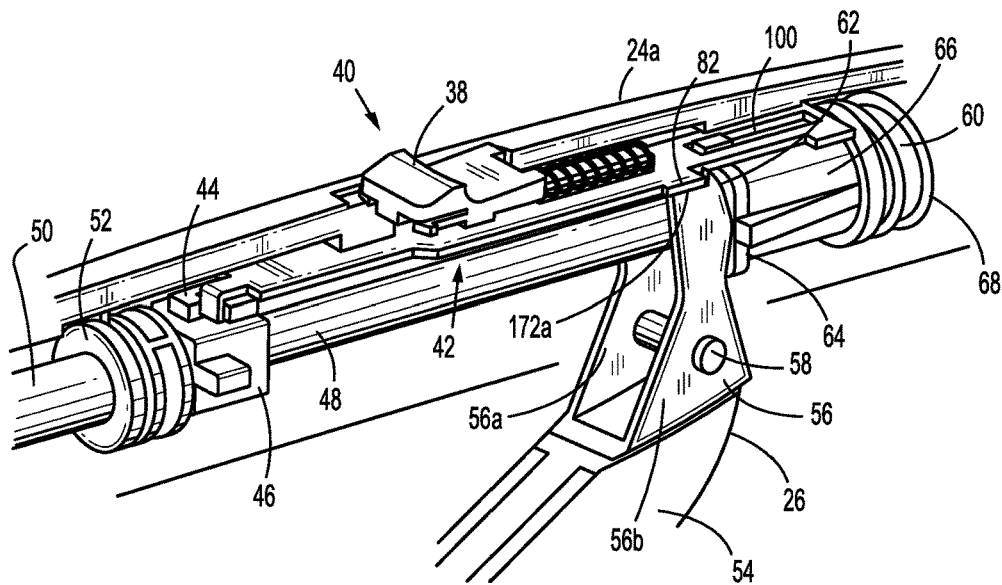
FIG. 2 is a perspective view of a body portion of the surgical stapling device with half of a handle housing removed and showing a lockout assembly.
FIG. 3 is a perspective view of the lockout assembly.
FIG. 3A is a perspective view, with parts separated, of the lockout assembly of FIG. 3.

Referring now to FIGS. 2-7, and initially with regard to FIGS. 2-3A, the auto-lock safety mechanism 40 includes switch 38, a primary lock or slider assembly 42 movably mounted within handle housing 24, a secondary lock or stopper 44 (FIG. 4) mounted in handle housing 24 and a cam member or block 46 which is affixed to a screw shaft assembly 48. The screw shaft assembly 48 is operably engaged with the approximation knob 28 at its proximal end (FIG. 1) and to the anvil assembly 20 at its distal such that the approximation knob 28 is actuable to move the anvil assembly 20 in relation to the shall assembly 22 as described below.

With specific reference to FIG. 2, screw shaft assembly 48 extends through an extension knob tube 50. The extension knob tube 50 supports a collar 52 that is rotatably mounted within the handle housing 24 and is connected to the approximation knob 28. As is known in the art (see the '106 patent), a proximal end of screw shaft assembly 48 includes a helical groove which receives a pin or projection (not shown) provided in the collar 52. Rotation of approximation knob 28, and thus extension knob tube 50 and collar 52, moves the pin within the helical groove in screw shaft assembly 48 to move screw shaft assembly 48 within the housing 24 proximally and distally relative to shell assembly 22.

Firing trigger 26 includes a lever 54 and an upright arm 56 that extends into the handle housing 24. Upright arm 56 may be formed as a pair of spaced upright arms 56a and 56b. A pivot pin 58 extends through upright arm 56 and is mounted to the handle housing 24 to allow firing trigger 26 to pivot relative to handle housing 24. An elongate, cylindrical pusher 60 extends through outer tube 16 (FIG. 1) from firing trigger 26 to shell assembly 22. Movement of firing trigger 26 toward handle housing 24 causes a distal edge 62 of each upright arm 56a, 56b to engage and drive a flange 64, located at a proximal end 66 of cylindrical pusher 60, distally to drive pusher 60 distally. As pusher 60 is driven distally within outer tube 16, a distal end (not shown) of pusher 60 drives the staples out of shell assembly 22 and into the staple clinching pockets of anvil assembly 20 to staple tissue captured between the shell assembly 22 and the anvil assembly 20. A coil spring 68 is provided around cylindrical pusher 60 between an inner wall of housing 24 and a surface of pusher 60 to bias the pusher 60 proximally within handle housing 24 and elongated outer tube 16. Biasing pusher 60 proximally, via engagement of flange 64 with arms 56a, 56b, urges firing trigger 26 towards the unfired position away from handle housing 24.

Referring now to FIGS. 3 and 3A, slider assembly 42 of auto-lock safety mechanism 40 is provided to initially block movement of firing trigger 26 until manually released and thereafter, automatically re-block firing trigger 26 after firing of the stapling device 10. This provides a higher degree of safety as compared to a manually actuated latch 32 which requires manual operation to reengage safety latch 32 after actuating the firing trigger 26. In addition to switch 38, slider assembly 42 includes a slider 70 and a spring 72 mounted on slider 70 which biases the slider 70 distally within handle housing 24 as will be discussed in further detail below. Slider 70 can be formed of sheet metal and includes a central body portion 74, a distal body portion 76 extending distally from central body portion 74 and a proximal body portion 78 extending proximally from central body portion 74. A downwardly depending arm or tab 80 extends from a proximal end of proximal body portion 78 and is received within secondary lock or stopper 44 (FIG. 2) as discussed in detail below to prevent movement of slider 70 within handle housing 24.

Central body portion 74 includes a pair laterally extending arms or trigger blocks 82, 84 at a distal end 86 of central body portion 74. Trigger blocks 82, 84 are positioned to engage flat surfaces 172a formed on upright arms 56a and 56b, respectively of firing trigger 26 to prevent movement of firing trigger 26 as described in more detail hereinbelow (see FIG. 14). Central body portion 74 additionally includes a proximally extending L-shaped mount 88 for fixedly supporting the switch 38 and a coil spring 72. The switch 38 can be fixedly secured to the slider 70 using any known fastening technique including gluing, welding, overmolding, etc. Mount 88 extends proximally along a centerline of central body portion 74 and includes an upright bar 90 and a longitudinal, proximally extending arm 92 extending from upright bar 90. Coil spring 72 is movably mounted over arm 92 and switch 38 is affixed to a proximal end 94 of arm 92. The coil spring 72 abuts a proximal side 98 of upright bar 90 and an inner surface (not shown) of the handle housing 24 to bias slider 70 and switch 38 distally within handle housing 24.

An elongate slot 100 extends longitudinally through distal body portion 76 from distal end 86 of central body portion 74 to a distal end 102 of distal body portion 76. Elongate slot 100 receives a protrusion 178 formed on pusher 60 such that when the pusher 60 is moved distally by the firing trigger 26, the slider 70 is pulled distally to disengage switch 38 from handle housing 24 in a manner described in detail below.

Switch 38 is affixed to mount 88 of slider 70 and includes a body portion 104 having an upwardly projecting distal finger tab 106 and a pair of distally extending latches 108, 110 extending from body portion 104 beneath finger tab 106. A notch 112 is formed in body portion 106. The switch 38 is movable to reposition the notch 112 to cover or uncover the indicator 34 (FIG. 1).

Figure 3B:
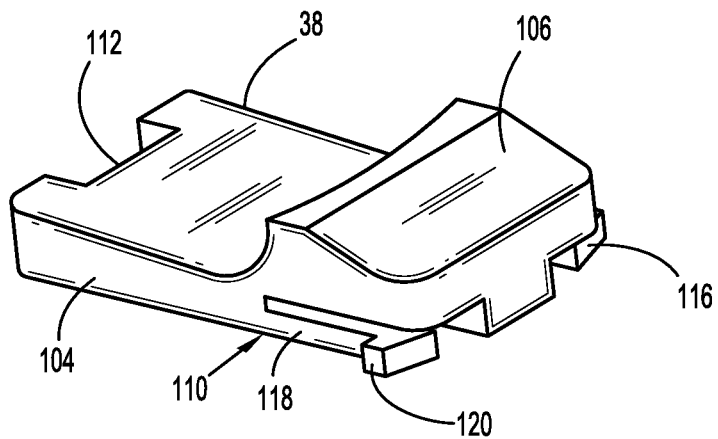
FIG. 3B is a perspective view of the safety button.

With specific reference to FIGS. 3-3B, latch 108 of switch 38 includes a flexible arm 114 that extends from body portion 104 and terminates in an outwardly extending tab 116 (FIGS. 3 and 3A). Similarly, latch 110 also includes a flexible arm 118 that extends from body portion 104 and terminates in an outwardly extending tab 120 (FIG. 3B). Tabs 116 and 118 releasably engage handle housing 24 and temporarily hold switch 38, and thus slider 70, in a proximal position to free up firing trigger 26 for actuation as will be described in further detail below.

Figure 4:
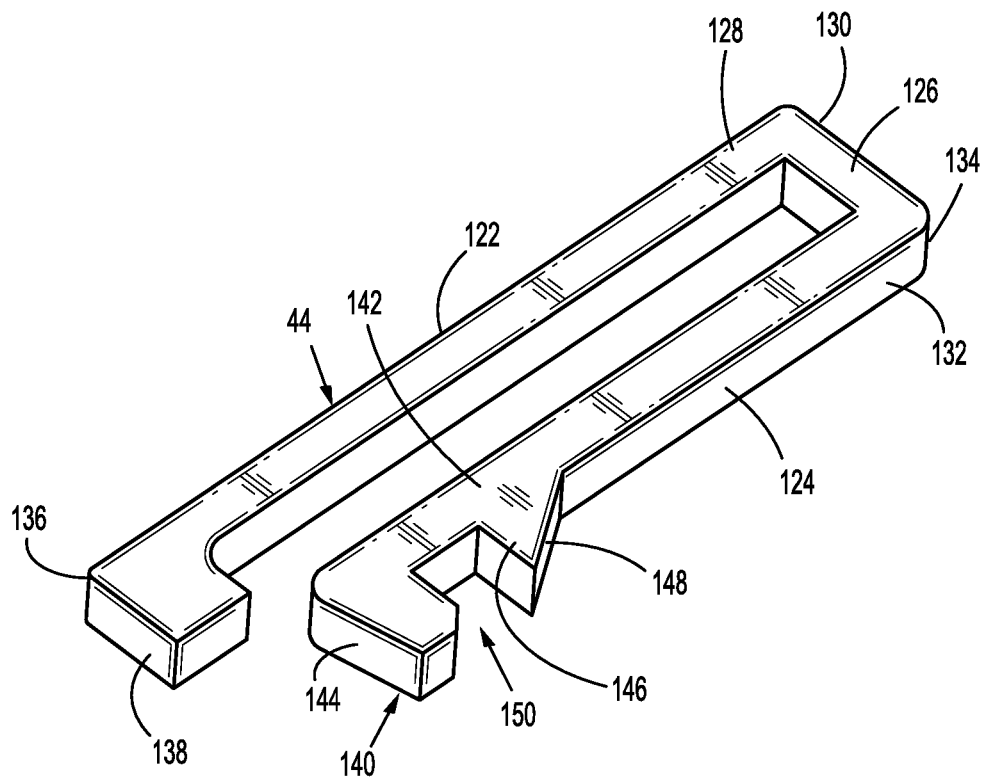
FIG. 4 is a perspective view of a secondary lockout member.

Referring to FIG. 4, stopper 44 is provided to prevent movement of slider 70 prior to the approximation of anvil assembly 20 with shell assembly 22. Stopper 44 is generally U-shaped and includes a first longitudinal bar 122, a second longitudinal bar 124 and a cross bar 126 flexibly connecting first longitudinal bar 122 to second longitudinal bar 124. Specifically, a distal end 128 of first longitudinal bar 122 is connected to a first end 130 of cross bar 126 and a distal end 132 of second longitudinal bar 124 is connected to a second end 134 of cross bar 126. In embodiments, first longitudinal bar 122, second longitudinal bar 124 and cross bar 126 may be formed integrally from a flexible material such as, for example, spring steel, polymeric materials, etc.

As shown, a proximal end 136 of first longitudinal bar 122 has an inwardly directed portion 138. Second longitudinal bar 124 is shorter than first longitudinal bar 122 and has a catch 140 formed at its proximal end 142. Catch 140 includes an inwardly directed portion 144 formed at proximal end 142 and a cam 146 formed on second longitudinal bar 124 distally of inwardly directed portion 142. Cam 146 has a distally facing, angled cam face 148. Catch 140 defines a gap 150 between inwardly directed portion 144 and cam 146 for receipt of tab 80 of slider 70.

Figures 5, 6:
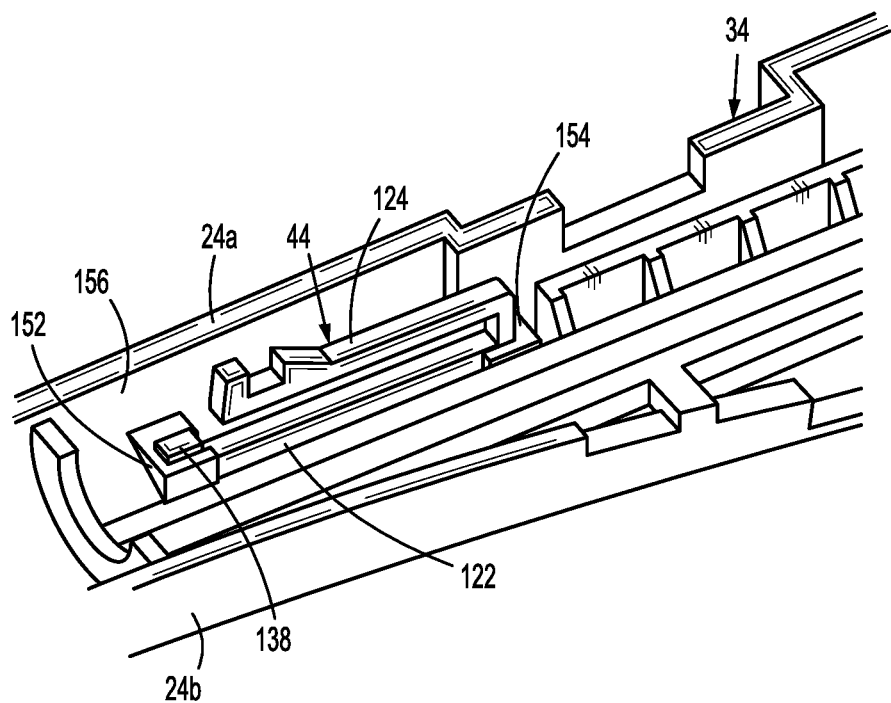
FIG. 5 is a perspective view of the secondary lockout member positioned within channel in a handle housing half.
FIG. 6 is a perspective view the handle housing half with a tab of a slider of the lockout assembly engaged with the secondary lockout member.

As best shown in FIG. 5, stopper 44 is supported within proximal and distal supports 152 and 154 formed within handle housing 24. The proximal and distal supports 152 and 154 extend inwardly from an inner surface 156 of handle housing half 24b. Specifically, inwardly directed portion 138 of first longitudinal bar 122 is located and frictionally retained within proximal support 152 while distal end 128 of first longitudinal bar 122 and first end 130 of cross bar 126 are frictionally retained within distal support 154. This leaves second longitudinal bar 124 free to flex downwardly relative to first longitudinal bar 122 to facilitate movement of catch 140 into and out of engagement with tab 80 of slider 70 as described in detail below.

Figure 7:
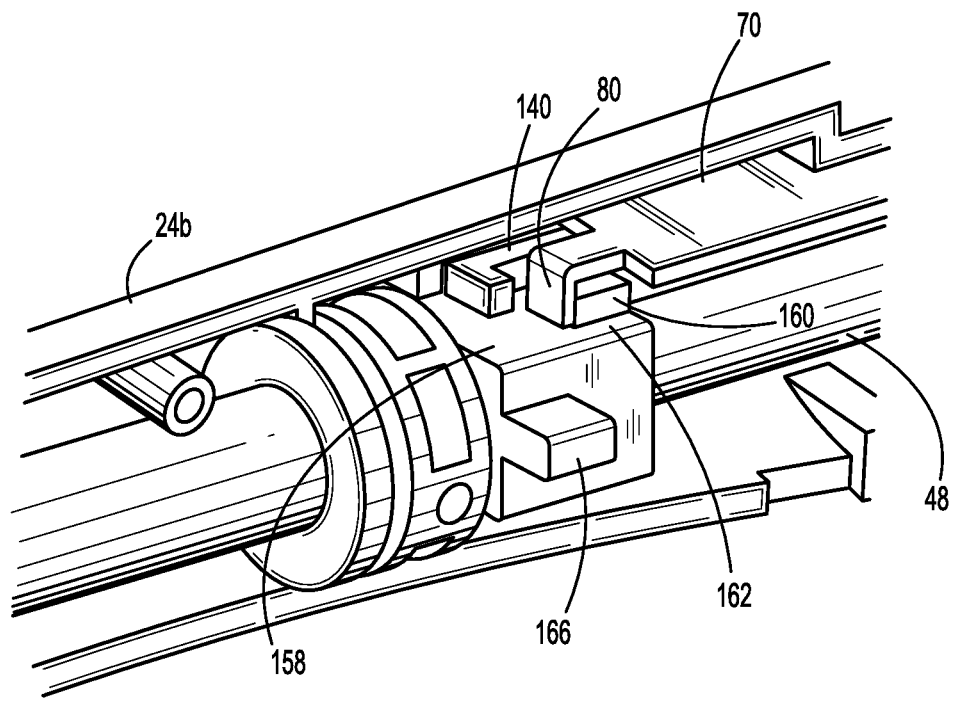
FIG. 7 is a perspective view similar to FIG. 6 with the secondary lockout member disengaged from the slider.
Figure 8:
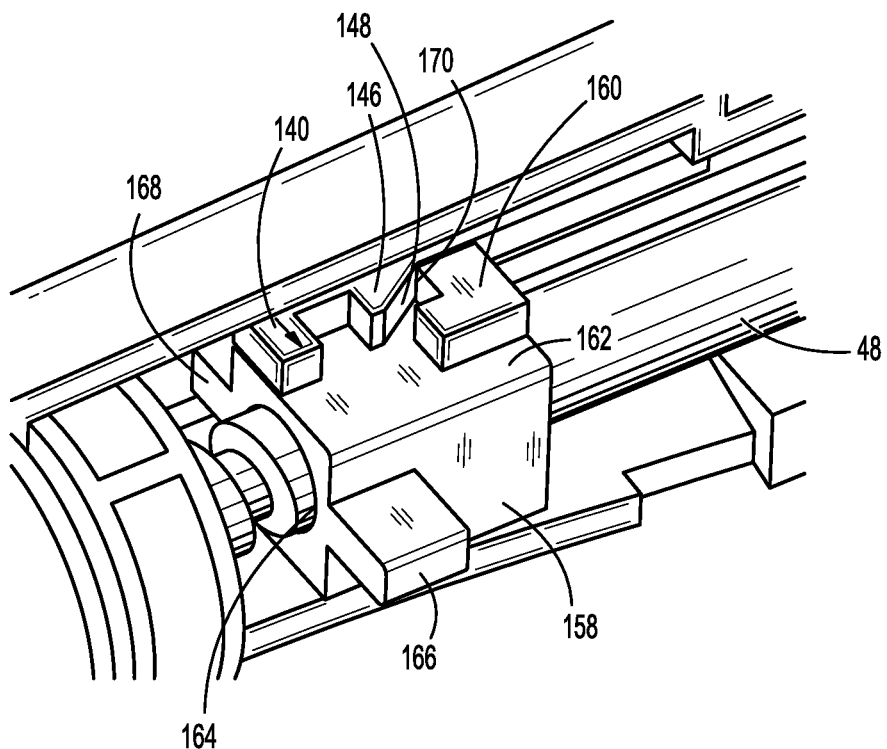
FIG. 8 is a perspective view of the a block, movable within the handle housing, engaging the secondary lockout member.

Referring now to FIGS. 6-8, in order to move or cam catch 140 out of engagement with tab 80 of slider 70, a block 158 having a projection 160 mounted on a first or upper surface 162 thereof is affixed to screw shaft assembly 48. Specifically, screw shaft assembly 48 passes through a bore 164 (FIG. 8) formed through block 158 and is fixedly secured to block 158 using, for example, a set screw (not shown). Thus, when the screw shaft assembly 48 is translated within the handle housing 24 via actuation of the approximation knob, block 158 translates within handle housing 24 along with screw shaft assembly 48. Block 158 additionally includes a pair of wings 166 and 168 which ride in corresponding channels (not shown) formed within handle housing halves 24a and 24b to guide movement of block 158 within the handle housing 24. As best shown in FIG. 8, projection 160 is generally L-shaped and has a proximal cam edge 170 which is positioned to engage the angled cam face 148 of cam 146 of stopper 44 to urge catch 140 outwardly to disengage tab 80 on slider 70 from the catch 40.

Referring now to FIGS. 1 and 6-15, the operation of auto-lock safety mechanism 40, including slider assembly 42 and stopper 44, will now be described. Referring to FIG. 1, trigger 26 is initially retained in a locked position by the trigger latch 32 which must be manually pivoted to an unlocked position. As noted hereinabove, trigger latch 32 is an optional feature of surgical stapling device 10 and is pivoted away from trigger 26 prior to use.

With reference also to FIG. 6, prior to approximation of the anvil assembly 20 in relation to the cartridge assembly 22, tab 80 of slider 70 is received within catch 140 of stopper 44 and block 158 is in a distal or advanced position with projection 160 of block 158 spaced distally of cam 146 of catch 140 of stopper 44. Engagement of tab 80 within the catch 140 prevents slider 70 from longitudinal movement within handle housing 24. Coil spring 72 (FIG. 11) is under compression and urges the slider 70 in the distal direction.

Referring briefly to FIG. 11, in the initial locked out position, trigger blocks 82 and 84 of slider 70, rest on upper flat surfaces 172a of upright arms 56a and 56b of trigger 26 to prevent pivotal movement of trigger 26. This internally "locks out" trigger 26 from actuation and firing of surgical stapling device 10.

Referring again to FIG. 1, when the anvil assembly 20 is approximated or moved proximally toward shell assembly 22 by rotating approximation knob 28 screw shaft assembly 48 is moved proximally within the handle housing 24. As the screw shaft assembly 48 is moved proximally, the block 158 is moved proximally within the handle housing 24.

Referring again to FIGS. 6-8, block 158 moves from its initial advanced position positioned distally of cam 146 of catch 140, wherein catch 140 of stopper 44 is engaged with tab 80 of slider 70 (FIG. 6), to a second position wherein proximal cam edge 170 of projection 160 on block 158 engages the angled cam face 148 of cam 146. As block 158 moves proximally, angled cam face 148 is moved laterally by proximal cam edge 170 to cam catch 140 of stopper 44 out of engagement with tab 80 on slider 70 (FIGS. 7 and 8). The release of tab 80 of slider 70 from catch 140 of stopper 44 frees up slider assembly 42 to facilitate manual movement of the switch 38 and, thus, slider assembly 42 along handle housing 24.

Referring for the moment to FIGS. 7, and 9-11, as screw shaft assembly 48 including block 158 is drawn proximally, projection 160 of block 158 engages tab 80 of slider 70 and pulls the slider assembly 42 proximally a short distance against the bias of the spring 72. As slider assembly 42 is moved proximally, firing trigger 26 is still locked out from movement by trigger blocks 82 and 84 of slider 70 which still partially engage flats 172a of upright arms 56a and 56b of the trigger 26. Switch 38, which is affixed to slider 70, also moves proximally a short distance. Switch 38 moves from an initial position wherein switch 38 covers indicator 34 (FIG. 9) to second position wherein indicator 34 is visible through notch 112 in switch 38 (FIG. 10). This gives a visual indication to a clinician that the anvil assembly 20 and shell assembly 22 are approximated and confirms that the slider assembly 42 has been released from stopper 44. Surgical stapling device 10 is now properly positioned about the tissues to be stapled.

Figure 12:
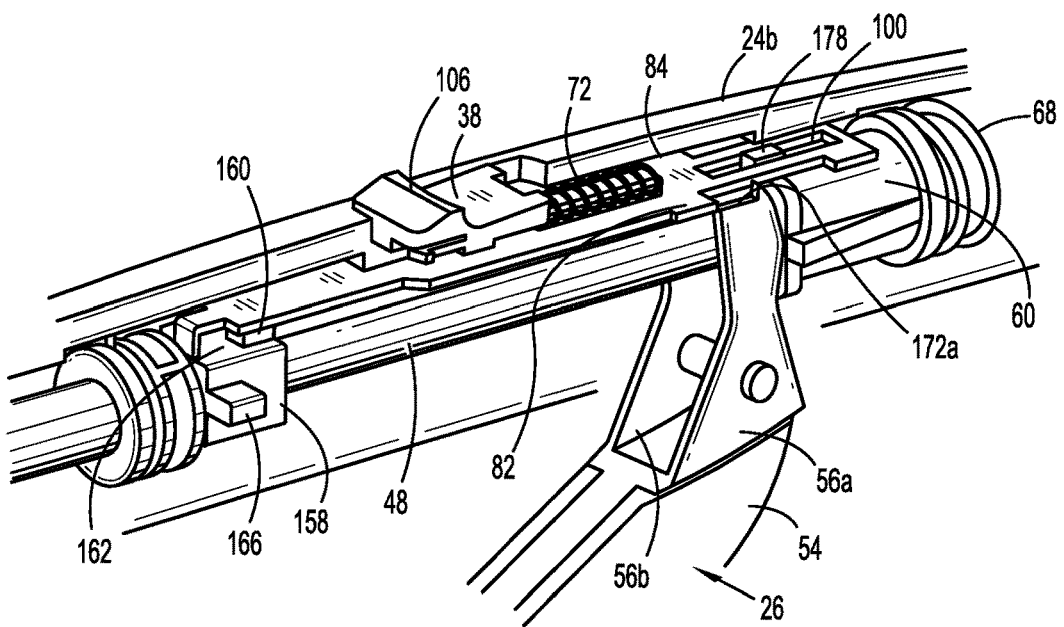
FIG. 12 is perspective view similar to FIG. 11, with the slider of the lockout assembly moved to release the trigger for actuation.
Figure 13:
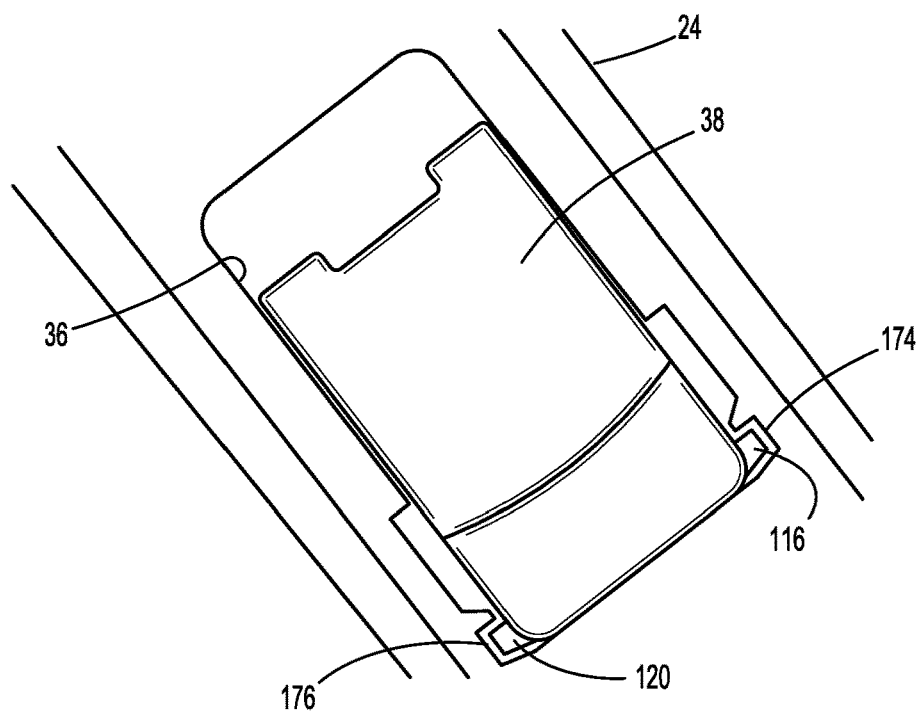
FIG. 13 is a top plan view of the safety button positioned within a window of the body portion and engaged in a locked position with the body portion.

Referring now to FIGS. 12-13, to release trigger 26 for actuation and firing of surgical stapling device 10, the operator pushes against finger tab 106 of switch 38 to move switch 38, and thus slider 70, proximally within handle housing 24 (FIG. 13). As slider 70 is drawn proximally, coil spring 72 is compressed and trigger blocks 82 and 84 are moved away from upper flat surfaces 172a of upright aims 56a and 56b of trigger 26 to unlock the trigger 26 for pivotal movement (FIG. 12).

As best shown in FIG. 13, when switch 38 is moved to its proximal-most position, the switch 38 and, thus, the slider 70 are retained in this position by tabs 116, 120. More specifically, switch 38 of slider assembly 42 is locked in a proximal most position by the outwardly extending tabs 116, 120 on flexible arms 114, 118 of switch 38 which snap into, notches 174 and 176, respectively, formed in handle housing 24 (FIG. 13) adjacent window 36. Receipt of tabs 116, 120 in notches 174, 176 maintains switch 38, and thus slider assembly 42, in the proximal position to maintain trigger blocks 82, 84 spaced from flat surfaces 172a of aims 56a, 56b, respectively of trigger 26 to maintain trigger 26 in the unlocked position.

Figure 14:
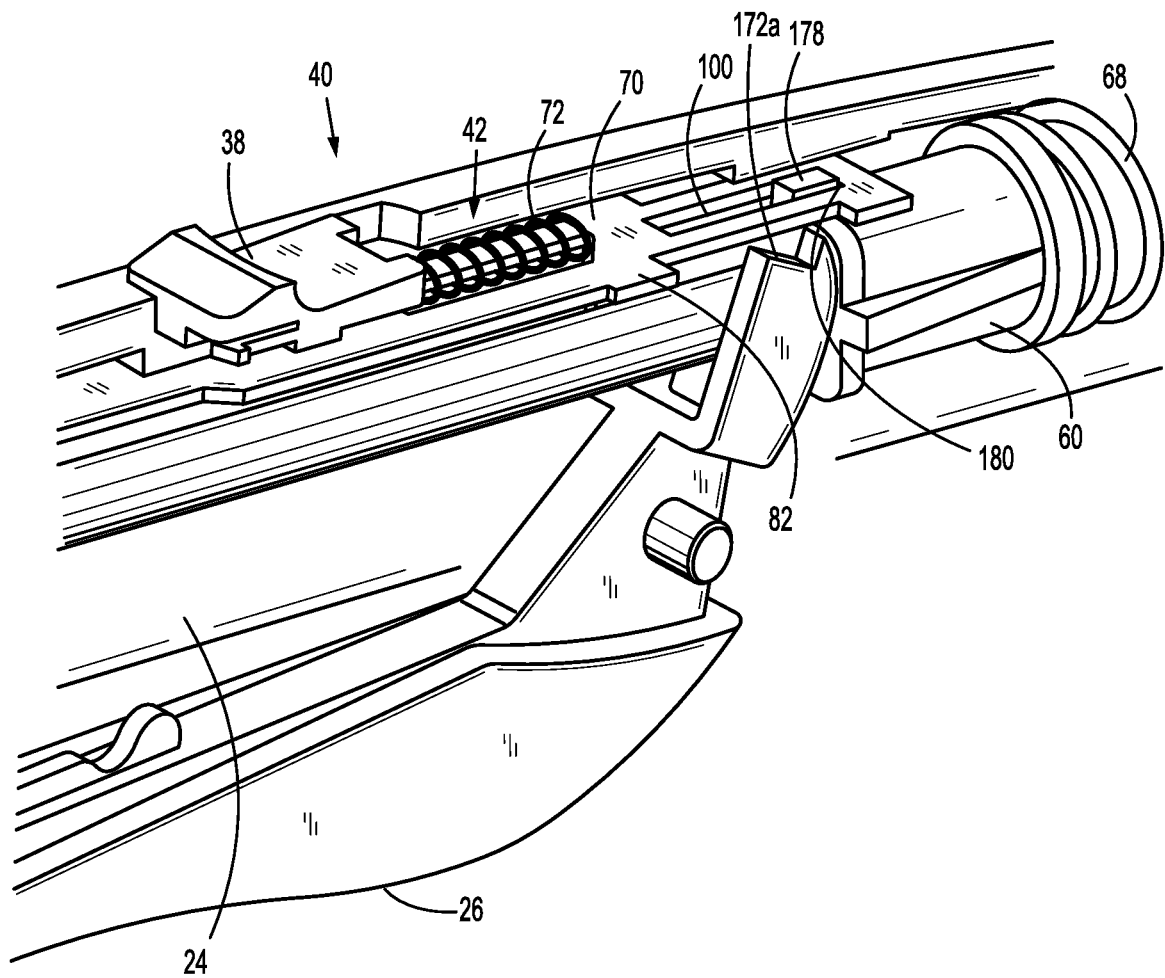
FIG. 14 is a perspective view of the trigger of the surgical stapling device engaging and driving a pusher of the surgical stapling device to fire the surgical stapling device.

As best shown in FIG. 14, in the unlocked position, the firing trigger 26 can be pivoted toward handle housing 24 to advance pusher 60, against the bias of coil spring 68, to fire staples from the shell assembly 22 through tissue and into anvil assembly 20.

Referring to FIG. 14, upon full actuation of trigger 26, primary slider lock assembly 42 is released to automatically re-lock out trigger 26 from a second actuation. More specifically, as pusher 60 is driven to a distal most position by trigger 26, a protrusion 178 formed on pusher 60 rides within elongated slot 100 in slider 70. As the distal most position of pusher 60 is reached and the staples have been formed against the anvil assembly 20, block 178 engages the portion of slider 70 defining a distal end 180 of elongated slot 100 to thereby pull slider 70 distally within handle housing 24. As slider 70 is pulled or forced distally, switch 38 is also forced distally such that the tabs 116 and 120 on flexible arms 114 and 118 of the switch 38 are released from locking notches 174 and 176 adjacent window 36 of handle housing 24. This frees up slider assembly 42 to move distally under the bias of coil spring 72. As the tabs 116 and 120 of switch 38 of slider assembly 42 are released from notches 174 and 176, the slider 70 snaps distally and makes a "click" sound giving an audible indication to the clinician that actuation of the trigger 26 is complete and that the auto-lock safety mechanism 40 of surgical stapling device 10 has been automatically reactivated. It is noted that movement of the switch 38 distally also provides a visual indication to the clinician that actuation of the trigger 26 is complete. Upon release of trigger 26, slider 70 returns to the initial position (FIG. 11) wherein slider 70 once again blocks trigger 26 from pivotal movement to prevent a second actuation of surgical stapling device 10.

It should be noted that, upon rotation of approximation knob 28 to separate anvil assembly 20 from shell assembly 22 and release the now stapled tissues, block 158 is moved distally to draw projection 160 out of engagement with catch 140 of stopper 44. Catch 140 flexes back into engagement with tab 80 on slider 70 to thereby again relock slider assembly 42 from further movement (FIG. 6).

Thus, in this manner, auto-lock safety mechanism 40 of surgical stapling 10 positively re-locks out trigger 26 from a second actuation after firing of surgical stapling device 10.

It will be understood that various modifications may be made to the embodiments disclosed herein. For example, the disclosed coil springs may be replaced with other types of springs, such as, for example, leaf springs, etc. Further, as noted above, the external trigger latch may be omitted. Therefore, the above description should not be construed as limiting, but merely as exemplifications of particular embodiments. Those skilled in the art will envision other modifications within the scope and spirit of the claims appended hereto.

The invention claimed is:

1. A surgical stapling device comprising:
a handle assembly including a stationary handle housing and a movable trigger mounted to the handle housing, the handle housing defining a window;
an elongated body portion extending from the handle housing;
a staple containing shell assembly mounted on a distal end of the elongated body portion and an anvil assembly movably mounted relative to the staple containing shell assembly;
an approximation mechanism operable to move the anvil assembly from a first position spaced from the staple containing shell assembly to a second approximated position adjacent the staple containing shell assembly;
a pusher extending through the elongated body portion from the handle housing to the staple containing shell assembly, the movable trigger being movable to drive the pusher distally to drive staples out of the staple containing shell assembly and into the anvil assembly; and
a slider assembly positioned within the handle housing including a slider, a biasing member, and a switch, the slider being longitudinally movable within the handle housing between a first position blocking the movable trigger from movement and a second position spaced from the movable trigger, the slider including at least one trigger block positioned to engage the movable trigger, the biasing member including a spring coil and being positioned to urge the slider towards the first position, the switch is fixedly attached to the slider and extends through the widow in the handle housing, wherein movement of the movable trigger towards the stationary handle housing causes the slider to move from the second position to the first position, wherein the slider includes a mount having an upright bar and a proximally extending arm, the switch being fixedly attached to a proximal end of the proximally extending arm and the coil spring being mounted around the proximally extending arm, the coil spring engaging the upright bar at a first end of the coil spring and engaging the handle housing at a second end of the coil spring.

2. The surgical stapling device as recited in claim 1, wherein the approximation mechanism includes a rotatable approximation knob mounted on the stationary handle housing and a screw shaft assembly extending from the approximation knob to the anvil assembly, the approximation mechanism being configured such that rotation of the approximation knob effects translation of the screw shaft assembly within the handle assembly.

3. The surgical stapling device as recited in claim 1, wherein the slider includes a mount having an upright bar and a proximally extending arm, the switch being fixedly attached to a proximal end of the proximally extending arm and the coil spring being mounted around the proximally extending arm, the coil spring engaging the upright bar at a first end of the coil spring and engaging the handle housing at a second end of the coil spring.

4. The surgical stapling device as recited in claim 1, wherein the switch includes at least one flexible latch that is configured to be received within a notch formed in an edge of the window in the handle housing when the slider assembly is in the second position to retain the slider assembly in the second position.

5. The surgical stapling device as recited in claim 4, wherein the slider includes a longitudinal slot and the pusher includes a protrusion movable within the longitudinal slot such that distal movement of the pusher effects distal movement of the protrusion into engagement with a distal end of the longitudinal slot to effect distal movement of the slider, wherein distal movement of the slider disengages the at least one flexible latch of the switch from the notch in the handle housing.

6. The surgical stapling device as recited in claim 1, wherein the switch defines a notch, the switch covering an indicator of the handle housing when the slider is in the first position and revealing the indicator of the handle housing when the switch is moved towards the second position.

\* \* \* \* \*